United States Patent

Hamstead et al.

[11] Patent Number: 5,359,897
[45] Date of Patent: Nov. 1, 1994

[54] APPARATUS FOR DETERMINING THE TIME TAKEN FOR SOUND ENERGY TO CROSS A BODY OF FLUID IN A PIPE

[75] Inventors: Peter J. Hamstead; Alan C. Smith, both of Herts, England

[73] Assignee: Front Engineering Ltd., Herts, England

[21] Appl. No.: 829,060
[22] PCT Filed: Aug. 8, 1990
[86] PCT No.: PCT/GB90/01242
§ 371 Date: Feb. 7, 1992
§ 102(e) Date: Feb. 7, 1992
[87] PCT Pub. No.: WO91/02246
PCT Pub. Date: Feb. 21, 1991

[30] Foreign Application Priority Data
Aug. 8, 1989 [GB] United Kingdom ............ 8918068.1

[51] Int. Cl.$^5$ .................. G01N 29/18; G01N 9/24
[52] U.S. Cl. ............................ 73/597; 73/32 A; 73/644; 73/64.53
[58] Field of Search .......... 73/597, 19.03, 24.01, 73/24.02, 24.03, 24.04, 24.05, 24.06, 32 A, 54.41, 61.49, 61.75, 61.79, 64.53, 861.27, 861.28, 861.29, 861.31, 644, 900

[56] References Cited

U.S. PATENT DOCUMENTS

| | | | |
|---|---|---|---|
| 2,708,366 | 5/1955 | Blocher et al. | 73/861.31 |
| 2,768,524 | 10/1956 | Beard | 73/54.41 |
| 3,468,157 | 9/1969 | Burk et al. | 73/24.01 |
| 4,004,461 | 1/1977 | Lynnworth | 73/861.27 |
| 4,015,464 | 4/1977 | Miller et al. | 73/61.75 |
| 4,255,964 | 3/1981 | Morison | 364/496 |

FOREIGN PATENT DOCUMENTS

| | | |
|---|---|---|
| 1291181 | 10/1972 | United Kingdom . |
| 1523231 | 8/1978 | United Kingdom . |
| 2009932 | 6/1979 | United Kingdom . |
| 2021768 | 12/1979 | United Kingdom . |
| 1579676 | 11/1980 | United Kingdom . |

Primary Examiner—John E. Chapman
Attorney, Agent, or Firm—Nixon & Vanderhye

[57] ABSTRACT

An apparatus for determining the time taken for sound energy to cross a body of fluid in a pipe uses a modified pipe in which flat members seal apertures in the pipe and two transducers are attached to respective flat members, wherein the material around each aperture curves away from the centre of the pipe towards the periphery of the aperture and contacts the respective flat member along the entire periphery of the aperture.

11 Claims, 2 Drawing Sheets

APPARATUS FOR DETERMINING THE TIME TAKEN FOR SOUND ENERGY TO CROSS A BODY OF FLUID IN A PIPE

BACKGROUND OF THE INVENTION

1. Field of the Invention

The present invention relates to an apparatus for determining the time taken for sound energy to cross a body of fluid in a pipe.

2. Related Art

The time taken for sound energy to cross a body of fluid in a pipe of known linear dimension in the direction of propagation of the sound energy provides a measure of the speed of sound in the fluid, and that can be used to determine a parameter of the fluid in the pipe, for example, the density of the fluid in the pipe. The determination of a parameter of a fluid may permit the identification of the fluid. For example, a measure of the speed of sound in a fluid which may be either beer or water may be used to distinguish between the fluids. Therefore, an apparatus for classifying fluids may be, in effect, an apparatus for measuring the speed of sound in the fluid.

BRIEF SUMMARY OF THE INVENTION

In accordance with the present invention, an apparatus for determining the time taken for sound energy to cross a body of fluid in a pipe includes a first electro-acoustic transducer which, in operation, sends sound energy through fluid in the pipe, a second electroacoustic transducer which, in operation, receives sound energy that has passed from the first electro-acoustic transducer through the fluid, electrical means for energising the first electro-acoustic transducer, and means for determining the difference between the time at which the first electro-acoustic transducer is energised and the time at which an electrical signal comes from the second electro-acoustic transducer in response to the transmitted acoustic signal, wherein the electro-acoustic transducers lie against respective substantially flat members which are positioned on opposite sides of the pipe and are substantially parallel to each other, which substantially flat members seal respective apertures in the pipe, wherein pipe material around each aperture curves away from the centre of the pipe towards the periphery of the aperture and contacts the respective substantially flat member along the entire periphery of the aperture.

Preferably, the pipe material around each aperture has a form generated by the forcing of a ball of hard material through a pilot opening in the pipe. It has been found that the curvature of the periphery of each aperture produced by the operation of forcing a ball of hard material through a pilot opening in the pipe is consistent with highly acceptable levels of noise from the flow of fluid past the aperture.

It has been found that the material around each aperture has a radius of curvature of the order of ½ inch, as a result of the operation for producing the aperture.

Preferably, the apertures are centred on a common diameter of the pipe.

Preferably, the means for determining the difference between the time at which the first electro-acoustic is energised and the time at which an electrical signal comes from the second electro-acoustic transducer, in response to the transmitted acoustic signal, includes delay means providing an electrical path with a delay equal to the interval between successive pulses from pulse generating means which energises the first electroacoustic transducer, and means for detecting when the leading edge of a pulse which passes through the delay means leaves the delay means before an electrical signal comes from the second electro-acoustic transducer.

Preferably, the apparatus includes means for setting the pulse generating means to its lowest frequency when the leading edge of a pulse which passes through the delay means leaves the delay means before an electrical signal comes from the second electro-acoustic transducer.

Preferably, the apparatus includes means for selecting a further electrical signal which comes from the second electro-acoustic transducer and is produced by sound energy which reaches the second electro-acoustic transducer after being reflected between the first and second electro-acoustic transducers, means for measuring the amplitude of the second electrical signal, and means for adjusting the the intensity of sound generated by the first electro-acoustic transducer in order to maintain the amplitude of the selected electrical signal at a set level.

The arrangement disclosed for mounting the transducers on the pipe provides transmitted sound pulses which result in received electrical pulses with significantly reduced distortion compared with the results obtained from attaching transducers to an unmodified pipe. It will be appreciated that any distortion of the received electrical pulse, especially distortion of the leading edge of the pulse, must degrade the potential accuracy of the final result, and the reduction of distortion compared with known systems represents an improvement over those systems.

The arrangement disclosed for mounting the transducers leads also to an improvement in signal levels over those obtained with an unmodified pipe, but it will be understood that improved signal levels alone would not improve the performance of an apparatus which operates with a significantly distorted received electrical signal, because of the loss of information represented by distorted pulse edges.

BRIEF DESCRIPTION OF THE DRAWINGS

An apparatus in accordance with the present invention will now be described, by way of example only, with reference to the accompanying drawings, in which.

DETAILED DESCRIPTION OF AN EXEMPLARY EMBODIMENT OF THE INVENTION

Figure 1:
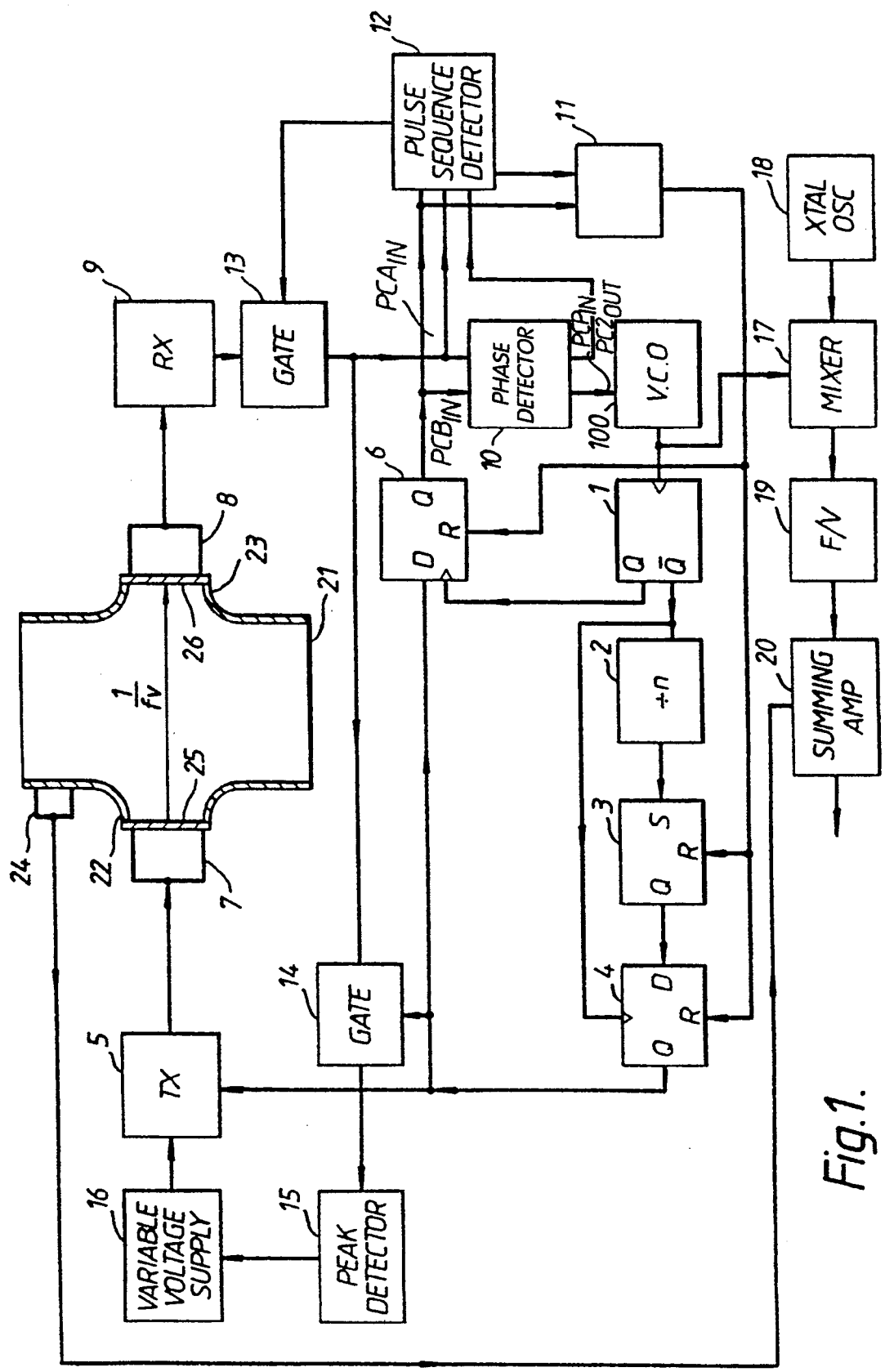
FIG. 1 is a block schematic representation of the apparatus including a modified pipe in accordance with the invention, and, FIG. 2 is block schematic representation of a pulse sequence detector circuit included in the apparatus represented by FIG. 1.

Referring to FIG. 1 of the accompanying drawings, an apparatus for determining the time taken for sound to cross a body of liquid in an enclosure, in this case a pipe 21, includes a voltage controlled oscillator (VCO) 100, a divider circuit 2, first, second, third, and fourth bistable flip-flops 1, 3, 4 and 6, a phase sensitive detector 10, first and second gating circuits 13 and 14, a pulse sequence detector 12, a further gating circuit 11, a peak voltage detector 15, a variable voltage supply 16, a transmitter stage 5, a receiver stage 9, first and second transducers 7 and 8, a crystal oscillator 18, a frequency mixing circuit 17, a frequency to voltage converting circuit 19, a summing amplifier 20, and a temperature sensor 24.

Referring to FIG. 1, the signal output port of the VCO 100 is connected to the CLOCK input port of the first bistable flip-flop 1, the inverted-signal ($\bar{Q}$) output port of the first bistable flip-flop 1 is connected to the signal input port of the divider circuit 2, the signal output port of the divider circuit 2 is connected to the SET input port of the second bistable flip-flop 3, the non-inverted signal (Q) output port of the second bistable flip-flop 3 is connected to the data (D) input port of the third bistable flip-flop 4, the non-inverted signal (Q) output port of the third bistable flip-flop 4 is connected to the signal input port of the transmitter stage 5, and the signal output port of the transmitter stage 5 is connected to the first transducer 7.

Referring still to FIG. 1, the signal output port of the second transducer 8 is connected to the signal input port of the receiver stage 9, the signal output port of the receiver stage 9 is connected to the signal input port of the first gating circuit 13, the signal output port of the first gating circuit 13 is connected to a first signal input port of the phase sensitive detector 10 and to the signal input port of the second gating circuit 14 and a first signal output port of the phase sensitive detector 10 is connected to the control input port of the VCO 100.

Referring still to FIG. 1, the inverted signal ($\bar{Q}$) output port of the first bistable flip-flop 1 is connected also to the CLOCK input port of the third bistable flip-flop 4, the non-inverted signal (Q) output port of the first bistable flip-flop 1 is connected to the CLOCK input port of the fourth bistable flip-flop 6, the non-inverted signal (Q) output port of the third bistable flip-flop 4 is connected also to the data (D) input port of the fourth bistable flip-flop 6 and to the gating input port of the second gating circuit 14, the non-inverted signal (Q) output port of the fourth bistable flip-flop 6 is connected to a second signal input port of the phase sensitive detector 10 and to a first signal input port of the pulse sequence detector 12, the signal output port of the first gating circuit 13 is connected to a second signal input port of the pulse sequence detector 12, a second signal output port of the phase sensitive detector 10 is connected to a third input signal port of the pulse sequence detector 12, a first signal output port of the pulse sequence detector 12 is connected to the gating input port of the second gating circuit 13, a second signal ouput port of the pulse sequence detector 12 is connected to a first signal input port of the gating circuit 11, the non-inverting signal (Q) output port of the fourth bistable flip-flop 6 is connected also to a second signal input port of the gating circuit 11, and the signal output port of the gating circuit 11 is connected to the RESET input ports of the second, third, and fourth bistable flip-flops 3, 4 and 6.

Referring still to FIG. 1, the signal output port of the VCO 100 is connected also to a first signal input port of the frequency mixing circuit 17 which has a second input port connected to the output port of the crystal oscillator 18, the signal output port of the frequency mixing circuit 17 is connected to the signal input port of the frequency to voltage converting circuit 19, the signal output port of the frequency to voltage converting circuit 19 is connected to a first signal input port of the summing amplifier 20 which has a second signal input port connected to the output port of the temperature sensor 24, and the signal output port of the summing amplifier 20 is connected to some form of display device (not shown).

Referring still to FIG. 1, the signal output port of the second gating circuit 14 is connected to the input port of the peak voltage detector 15, the output port of the peak voltage detector 15 is connected to a control input port of the variable voltage supply 16, and the supply output port of the variable voltage supply 16 is connected to the supply voltage port of the transmitter stage 5.

As shown in FIG. 1 of the accompanying drawings, the transducers 7 and 8 are attached to flat members 25 and 26 which seal apertures centred on a common diameter of the pipe 21, which is cylindrical. The flat members 25 and 26 contact the pipe along the entire respective peripheries of the apertures and are welded to the pipe. The pipe material provides the peripheries of the apertures. The pipe material around each of the apertures curves away from the centre of the pipe towards the periphery of the aperture.

The section of pipe presented in FIG. 1 is produced by cutting a slot at the position of each aperture in the pipe 21, inserting a steel ball into the pipe 21, and forcing the steel ball through the slot by pulling it through the slot. After the slot has been expanded into an aperture, the edges of the apertures are machined to bring them level with the pipe profile and to make them substantially parallel, and the flat members 25 and 26 are welded to the pipe 21. It has been found that when the operation is performed on a 3" stainless steel pipe of 16 gauge to produce an aperture with a 1½" outside diameter, beginning with a ½" slot, the radius of curvature of the pipe material bounding the aperture is ½".

The results obtained with the section of pipe represented in FIG. 1 is significantly better than that obtained when transducers are attached to an unmodified section of pipe. Not only is the level of the received acoustic signal improved in the modified pipe in relation to the unmodified pipe, but also, a transmitted sound pulse leads to a received electrical pulse with substantially less distortion than is the case with the unmodified pipe. It will be evident that any significant distortion of the electrical pulse obtained from the received acoustic pulse, especially distortion of the leading edge of the pulse, will lead to inaccurate results from apparatus intended to measure the transit time of a sound pulse across a pipe.

The reason for the improved shape of the received electrical pulse obtained with the modified pipe over that obtained with the unmodified pipe is not fully understood, but is believed to be due to the fact that the modified pipe transmits less of the sound energy along its walls than does the unmodified pipe. Certain alternative modifications of the pipe, such as the machining of flat surfaces on the walls of a pipe (thickened walls may be necessary) or the provision of solid stubs with flat faces for the transducers, do not provide any significant improvement over the performance of an unmodified pipe.

The apparatus represented by FIG. 1 operates as follows:

The VCO 100 generates pulses at a rate fv pulses per second, that is, with a period 1/fv seconds, and the pulse stream produced by the VCO 100 is operated on by the first bistable flip-flop which produces a symmetrical waveform (50% duty factor) in which the successive rising and falling edges occur at intervals of 1/fv seconds. The inverted signal ($\overline{Q}$) and the non-inverted signal (Q) outputs from the first bistable flip-flop 1 are in antiphase, which means that the rising edges of the non-inverted signal (Q) and the inverted signal ($\overline{Q}$) occur alternately at intervals of 1/fv seconds. The inverted signal ($\overline{Q}$) is applied to the divider circuit 2 which counts the rising edges of the applied signal and, when the count reaches n, the divider changes its output signal level from a logical o to a logical 1 that is, the count of n is marked by a positive step in the output signal from the divider circuit 2 and the positive step coincides with a rising edge of the signal $\overline{Q}$ from the first bistable flip-flop 1. The output signal from the divider circuit 2, applied to the SET input port of the second bistable flip-flop 3, has the effect of making its Q output signal a logical 1 when the dividing circuit 2 provides a logical 1 output.

Still referring to the operation of the apparatus represented by FIG. 1 of the accompanying drawings, the third bistable flip-flop 4 is forced to change its output Q from a logical Q to a logical 1 when its data (D) input port receives the logical 1 signal from the Q output port of the second bistable flip-flop 3, since, at that time, the Q output port of the first bistable flip-flop 1 will provide a signal with a rising edge at the CLOCK input port of the third bistable flip-flop 4. The abrupt voltage change occurring at the Q-output of the third bistable flip-flop 4 energises the transducer 7 by way of the transmitter stage 5. The transmitter stage 5 is caused to oscillate by the abrupt voltage change applied to it and drives the transducer 7, launching a burst of sound across the fluid in the pipe 21. The sound is received by the transducer 8 which converts the sound to an electrical signal and passes that to the receiver stage 9. The leading edge of the electrical signal passed on by the receiving stage 9 is, of course, delayed relative to the abrupt voltage transition provided by the Q output of the third bistable flip-flop 4 by a time equal to that required for the sound to travel through the fluid separating the transducers 7 and 8. The electrical signal passed on by the receiver stage 9 passes through the gating circuit 13 to the phase sensitive detector 10.

Still referring to the operation of the apparatus represented by FIG. 1 of the accompanying drawings, after the abrupt rise in voltage that occurs at the output port Q of the third bistable flip-flop 4, that voltage remains at the logical 1 level until the output of the divider circuit 2 changes to the logical 0 level or the third bistable flip-flop 4 is reset. On the rise in the voltage at the Q output port Q of the third bistable flop 4, the D input port of the fourth bistable flip-flop 6 will be held at the logical 1 level because of its connection to the Q output port of the third bistable flip-flop 6, and that logical 1 level will be transferred to the Q output of the fourth bistable flip-flop 6 on the rising edge of the next pulse from the VCO 100 because the rising edges generated by the Q output of the first bistable flip-flop 1 coincide with the rising edges of the pulses from the VCO 100. The abrupt rise in the voltage at the Q output of the fourth bistable flip-flop 6 is communicated also to an input port of the phase sensitive detector 10 (as has been explained above, a pulse passing through the gate 13 is another signal communicated to an input port of the phase sensitive detector 10).

Referring still to the operation of the apparatus represented by FIG. 1 of the accompanying drawings, the phase sensitive detector 10 is a part of a Type CD 4046 integrated circuit capable of providing output signals indicating whether the leading edges of the two signals applied to it are in phase or not in phase, another part of the Type CD 4046 integrated circuit being the VCO 100 itself, and the phase sensitive detector 10 is capable also of providing signals for adjusting the frequency and phase of the VCO 100. The phase sensitive detector 10 responds to the relative positions of the leading edges of the signals reaching it by way of the fourth bistable flip-flop 6 and the gate 13 as follows:

If the leading edges of the two signals presented to It are in phase, the phase sensitive detector 10 effectively disconnects itself from the VCO 100, leaving the VCO 100 undisturbed, and provides a logical 1 output voltage on the connection to the pulse sequence detector 12.

If the leading edges of the two signals presented the phase sensitive detector 10 are not in phase, it remains connected to the VCO 100 and provides a logical 1 or logical 0 signal, according to which signal leading, for effecting a change in the frequency of the VCO 100 in a sense that would reduce the phase difference between the leading edges of the two input signals, and also provides a logical Q output voltage in the connection to the pulse sequence detector 12.

Still referring to the operation of the apparatus represented by FIG. 1 of the accompanying drawings, the abrupt change in the voltage at the output Q of the fourth bistable flip-flop 6 is conditioned by the gating circuit 11 and used to reset the flip-flops 3, 4 and 6, after which another electrical pulse will, in due course, be supplied by the transmitter stage 5 by the third bistable flip-flop 4, and so on.

Still referring to the operation of the apparatus represented by FIG. 1 of the accompanying drawings, the apparatus may be expected to settle to a stable condition in which the rising edges of the signals arriving at the input ports of the phase sensitive. detector 10 are in phase for most of the time, and the VCO 100 operates at a constant frequency, the period of which is then equal to the time taken for a burst of sound to cross the body of fluid separating the transducers 7 and 8. It will be understood that the burst of sound will be converted into an electrical signal by the tranducer 8, and that the electrical signal provided by the transducer 8 will have the form of a damped oscillation. The receiver stage 9 which receives the electrical signal from the transducer 8 carries out the function of selecting the first half cycle of the electrical signal from the transducer 8 (that is, the first half cycle of the damped oscillation), amplifying it, and clipping it to provide a pulse suitable for application to the phase sensitive detector 10.

Referring further to the operation of the apparatus represented by FIG. 1 of the accompanying drawings, the level of the electrical signal reaching the receiver stage 9 is controlled by the combined action of the gate 14, the peak voltage detector 15, and the variable voltage supply 16. When the transducer 7 produces a burst of sound, some of that sound will be reflected at the transducer 8, return towards the transducer 7, and be reflected by the transducer 7, returning to the transducer 8 some 3/fv seconds after the burst of sound was produced by the transducer 7, when the VCO 100 is stable and operating at a frequency fv. The sound arriving at the transducer 8 at a time 3/fv seconds after the second burst was produced by the transducer 7 is converted to an electrical signal by the transducer 8, and that electrical signal is selected by opening the gate 14 for the period between 2/fv and 4/fv seconds following the change in voltage of the Q output of the third flip-flop 4 from logical Q to logical 1, which may be achieved by means of monostable flip-flops included in the gate circuit 14. The peak voltage detector 15 effects measurement of the peak voltage of the electrical signal passed on by the gate circuit 14, and the output signal from the peak voltage detector 15 is used to control the variable voltage supply 16, the sense of the control being such as to maintain a relatively constant level of electrical signal passing through the gate circuit 14. The stabilization of the level of electrical signal passing through the gate circuit 14 results in the stabilization of the level of electrical signals applied to the phase sensitive detector 10 by way of the receiver 9 and gate circuit 13. The performance of the apparatus is improved by the inclusion of the system for stabilizing the level of the electrical signal which passes through the gate 13 at about 1/fv seconds after the change in voltage of the Q output of the third flip-flop 4 from logical Q to logical 1.

Referring still to the operation of the apparatus represented by FIG. 1 of the accompanying drawings, the signal from the VCO 100 is applied to the frequency mixing circuit 17 along with the signal from the crystal oscillator 18, producing a signal with frequency within the range of the frequency to voltage converting circuit 19 which then provides an output voltage indicative of the frequency of the VCO 100. That voltage is adjusted in amplitude by an amount dependent on the temperature of the fluid, as signalled by the temperature sensor 24 to the summing amplifier 20. The output of the summing amplifier 20 may be converted into any one of several forms of display data, including, for example, an indication of what fluid occupies the pipe 21.

Referring still to the operation of the apparatus represented by FIG. 1 of the accompanying drawings, the pulse sequence detector 12 is provided with input signals $PCB_{in}$, having a waveform with a rising edge followed by a logical 1 level, $PCA_{in}$, having a waveform similar to that of $PCB_{in}$, and $PCP_{out}$, having a waveform that has a logical 1 value when the leading edges of $PCB_{in}$ and $PCA_{in}$ coincide, and having a waveform that falls from the logical 1 valve to a logical Q valve during any period when only $PCB_{in}$ or $PCA_{in}$ is present. The signals applied to the pulse sequence detector 12 are, therefore, capable of indicating whether the VCO 100 is "in lock", that is, the rising edges of $PCB_{in}$ and $PCA_{in}$ are coincident, or "out of lock" with either the rising edge of $PCB_{in}$ occurring first on the rising edge of $PCA_{in}$ occurring first. The pulse sequence detector 12 provides no output when the VCO 100 is "in lock" blocks the signal through the gating circuit 13 when the rising edge of $PCB_{in}$ occurs first, and resets the second, third and fourth bistable flip-flops 3, 4 and 6 by way of the gating circuit 11 when the leading edge of $PCA_{in}$ occurs first. The effect of the pulse sequence detector 12 blocking the signal passing through the gating circuit 13 is that the phase sensitive detector 10 is provided with only the signal $PCB_{in}$ and responds by causing the VCO 100 to move to its lowest operating frequency, thereby ensuring that the VCO 100 will not be left operating at too high a frequency for any length of time.

Figure 2:
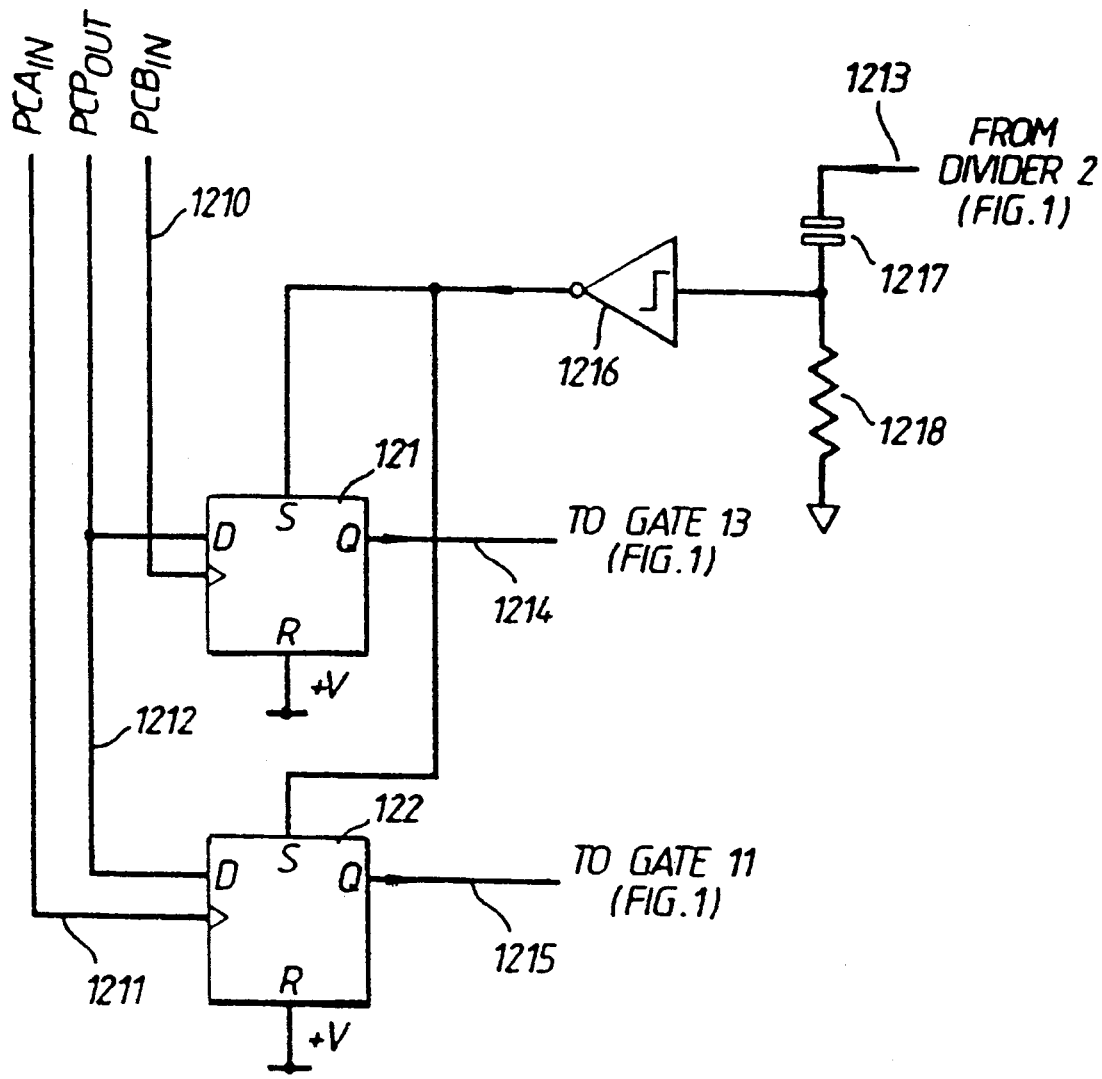

A more detailed diagrammatic representation of the pulse sequence detector 12 is given by FIG. 2 of the accompanying drawings, which more detailed representation shows that the pulse sequence detector includes bistable flip-flops 121 and 122, an inverting circuit 1216, and a differentiating network consisting of a capacitor 1217 and a resistor 1218. The flip-flops 121 and 122 are D-type devices having there D input ports connected together and connected to receive the $PCP_{out}$ signal from the phase sensitive detector 10 of FIG. 1 on a connection 1212. The clock input port of the flip-flops 121 is connected, by way of a connector 1210, to receive the $PCB_{in}$ signal of the phase sensitive detector 10 of FIG. 1, and the clock input port of the flip-flop 122 is connected, by way of a connector 1211, to receive the $PCA_{in}$ signal of the phase sensitive detector 10 of FIG. 1. The SET input ports of the flip-flops 121 and 122 are connected together and to the output port of the inverting circuit 1216. The input port of the inverting circuit 1216 is connected to the junction of the capacitor 1217 and the resistor 1218, and the terminal of the capacitor 1218 that is remote from the resistor 1218 is connected to the output of the dividing circuit 20 of FIG. 1, by way of a connector 1213. It should be noted here that the connection of the pulse sequence detector 12 to the dividing circuit 2 is not actually shown in FIG. 1. The Q output ports of the flip-flops 121 and 122 are connected, respectively, to the gating circuits 13 and 11 by way of connectors 1214 and 1215.

The circuit represented by FIG. 2 operates as follows:

When the divider circuit 2 provides an output signal with a rising edge, the flip-flops 121 and 122 are set by way of the connector 1213, the capacitor-resistor network 1217, 1218 and the inverting circuit 1216.

Following the occurrence of the output signal with a rising edge from the dividing circuit 2, of FIG. 1, signals $PCA_{in}$, $PCP_{out}$, and $PCB_{in}$ appear on the connectors 1211, 1212, and 1210. When the VCO 100, of FIG. 1, is "in lock" the signal $PCP_{out}$ has a logical 1 value and the signals $PCA_{in}$ and $PCB_{in}$ have leading edges occurring at the same time, resulting in the flip-flops 121 and 122 being clocked simultaneously by the signals $PCA_{in}$ and $PCB_{in}$, and logical i outputs appearing at both Q outputs of the flip-flops 121 and 122. When the leading edge of the signal $PCB_{in}$ occurs before that of $PCA_{in}$ the flip-flop 121 is clocked by $PCB_{in}$ while the signal $PCP_{out}$ is still high and a logical 1 is loaded into the flip-flop 121, whereas a logical Q is loaded into the flip-flop 122. The situation is reversed when the leading edge of $PCA_{in}$ occurs before that of $PCB_{in}$, and the flip-flop 122 is loaded with a logical 1 while the flip-lop 121 is loaded with a logical 0. The Q output of the flip-flops 121 and 122, therefore, indicate the time relationships of the leading edges of the signals $PCA_{in}$ and $PCB_{in}$.

We claim:

1. An apparatus for determining the time taken for sound energy to cross a body of fluid in a pipe, including:

a first electro-acoustic transducer which, in operation, sends sound energy through fluid in the pipe, a second electro-acoustic transducer which, in operation, receives sound energy that has passed from the first electro-acoustic transducer through the fluid, electrical means for energizing the first electro-acoustic transducer, means for determining the difference between the time at which the first electro-acoustic transducer is energized and the time at which an electrical signal comes from the second electro-acoustic transducer in response to the transmitted acoustic signal, and said electro-acoustic transducers being disposed against respective substantially flat members which are positioned on opposite sides of the pipe and are substantially parallel to each other, which substantially flat members seal respective apertures in the pipe, wherein pipe material around each aperture curves away from the center of the pipe towards the periphery of the aperture and contacts the respective substantially flat member along the entire periphery of the aperture.

2. An apparatus as in claim 1, wherein the the pipe material around each aperture has a form generated by forcing a ball of hard material through a slot in the pipe.

3. An apparatus as in claim 2, wherein the material around each aperture has a radius of curvature of the order of ½ inch.

4. An apparatus for determining the time taken for sound energy to cross a body of fluid in a pipe, including:
- a first electro-acoustic transducer which, in operation, sends sound energy through fluid in the pipe,
- a second electro-acoustic transducer which, in operation, receives sound energy that has passed from the first electro-acoustic transducer through the fluid,
- electrical means for energizing the first electro-acoustic transducer,
- means for determining the difference between the time at which the first electro-acoustic transducer is energized and the time at which an electrical signal comes from the second electro-acoustic transducer in response to the transmitted acoustic signal, and
- said electro-acoustic transducers being disposed against respective substantially flat members which are positioned on opposite sides of the pipe and are substantially parallel to each other, which substantially flat members seal respective apertures in the pipe, wherein pipe material around each aperture curves away from the center of the pipe towards the periphery of the aperture and contacts the respective substantially flat member along the entire periphery of the aperture,
- wherein the apertures are centered on a common diameter of the pipe.

5. An apparatus as in claim 1, wherein the means for determining the difference between the time at which the first electro-acoustic transducer is energized and the time at which an electrical signal comes from the second electro-acoustic transducer, in response to the transmitted acoustic signal, includes:
- delay means providing an electrical path with a delay equal to the interval between successive pulses from pulse generating means which serves as a clock generator for means which energizes the first electro-acoustic transducer, and
- means for detecting when the leading edge of a pulse which passes through the delay means leaves the delay means before an electrical signal comes from the second electroacoustic transducer.

6. An apparatus as claimed in claim 5, which includes means for setting the pulse generating means to its lowest frequency when the leading edge of a pulse which passes through the delay means leaves the delay means before an electrical signal comes from the second electro-acoustic transducer.

7. An apparatus for determining the time taken for sound energy to cross a body of fluid in a pipe, including:
- a first electro-acoustic transducer which, in operation, sends sound energy through fluid in the pipe,
- a second electro-acoustic transducer which, in operation, receives sound energy that has passed from the first electro-acoustic transducer through the fluid;
- electrical means for energizing the first electro-acoustic transducer,
- means for determining the difference between the time at which the first electro-acoustic transducer is energized and the time at which an electrical signal the second electro-acoustic transducer in response to the transmitted acoustic signal
- said electro-acoustic transducers being disposed against respective substantially flat members which are positioned on opposite sides of the pipe and are substantially parallel to each other, which substantially flat members seal respective apertures in the pipe, wherein pipe material around each aperture curves away from the center of the pipe towards the periphery of the aperture and contacts the respective substantially flat member along the entire periphery of the aperture;
- means for selecting a further electrical signal which comes from the second electro-acoustic transducer and is produced by sound energy which reaches the second electro-acoustic transducer after being reflected between the first and second electro-acoustic transducers,
- means for measuring the amplitude of the second electrical signal, and
- means for adjusting the intensity of sound generated by the first electroacoustic transducer in order to maintain the amplitude of the selected electrical signal at a set level.

8. In an acoustic signal velocity measuring system having transmitting and receiving transducers mounted on opposite sides of a flowing fluid conduit, the improvement comprising:
- a first transducer disposed adjacent a first fiat portion of said conduit, said first fiat portion being disposed outwardly from the conduit wall surface and integrally connected therewith by curved transition walls;
- a second transducer disposed adjacent a second flat portion of said conduit opposite said first portion, said second fiat portion also being disposed outwardly from the conduit wall surface and integrally connected therewith by curved transition walls; and
- means for measuring acoustic velocity connected to said first and second transducers.

9. In an acoustic signal velocity measuring system as in claim 8 wherein said transducers are mounted on opposite sides or a flowing fluid conduit, and including:
- a pair of transducer ports opposingly disposed along an extended diameter of said conduit and integrally formed by outwardly curved side wall portions of the conduit.

10. An improved acoustic signal velocity measuring system as in claim 9 wherein:
- said conduit nominally has a circular cross-section of diameter D;
- said transducer ports each have a nominally circular cross-section of diameter d which is substantially less than D; and
- said curved sidewall portions have a radius of curvature R.

11. An improved acoustic signal velocity measuring system as in claim 10 wherein D, d and R have approximate relative dimensions of 6, 3 and 1 respectively.

* * * * *